(12) United States Patent
Sarge

(10) Patent No.: US 9,603,615 B2
(45) Date of Patent: Mar. 28, 2017

(54) VASCULAR RE-ENTRY DEVICE

(75) Inventor: Jeff Sarge, Fremont, CA (US)

(73) Assignee: C.R. Bard, Inc., Murray Hill, NJ (US)

( * ) Notice: Subject to any disclaimer, the term of this patent is extended or adjusted under 35 U.S.C. 154(b) by 263 days.

(21) Appl. No.: 14/365,016

(22) PCT Filed: Jan. 18, 2012

(86) PCT No.: PCT/US2012/021766
§ 371 (c)(1),
(2), (4) Date: Oct. 8, 2014

(87) PCT Pub. No.: WO2013/109269
PCT Pub. Date: Jul. 25, 2013

(65) Prior Publication Data
US 2015/0039004 A1    Feb. 5, 2015

(51) Int. Cl.
| | |
|---|---|
| *A61B 17/32* | (2006.01) |
| *A61M 29/00* | (2006.01) |
| *A61B 17/22* | (2006.01) |
| *A61F 2/958* | (2013.01) |
| *A61B 50/13* | (2016.01) |
| *A61B 17/00* | (2006.01) |

(52) U.S. Cl.
CPC ........ *A61B 17/320068* (2013.01); *A61B 17/22012* (2013.01); *A61B 50/13* (2016.02); *A61F 2/958* (2013.01); *A61M 29/00* (2013.01); *A61B 2017/003* (2013.01); *A61B 2017/00778* (2013.01); *A61B 2017/22014* (2013.01); *A61B 2017/22095* (2013.01); *A61F 2250/0093* (2013.01)

(58) Field of Classification Search
CPC ...... A61B 17/320068; A61B 17/22012; A61B 2017/00778; A61B 2017/22014; A61B 2017/003; A61B 2017/22095; A61M 29/00; A61F 2/958; A61F 2250/0093
See application file for complete search history.

(56) References Cited

U.S. PATENT DOCUMENTS

| | | | |
|---|---|---|---|
| 6,190,353 B1 * | 2/2001 | Makower | A61B 1/3137 600/137 |
| 6,514,249 B1 * | 2/2003 | Maguire | A61B 18/00 606/37 |
| 8,768,433 B2 * | 7/2014 | Jenkins | A61B 5/055 600/410 |

* cited by examiner

*Primary Examiner* — Julian W Woo
(74) *Attorney, Agent, or Firm* — C.R. Bard Intellectual Property

(57) ABSTRACT

An ultrasonic device having a tri-axial configuration including an ultrasound transmission member, a dilator, and a sheath is disclosed. The ultrasound device may be used in a procedure to treat an occluded blood vessel. The ultrasound transmission member can transmit ultrasonic energy from an ultrasonic transducer to a distal end. The dilator facilitates entry of the ultrasonic transmission member into the subintimal space of a blood vessel. The sheath may articulate to aid in the process of re-entering the central lumen of the blood vessel.

9 Claims, 17 Drawing Sheets

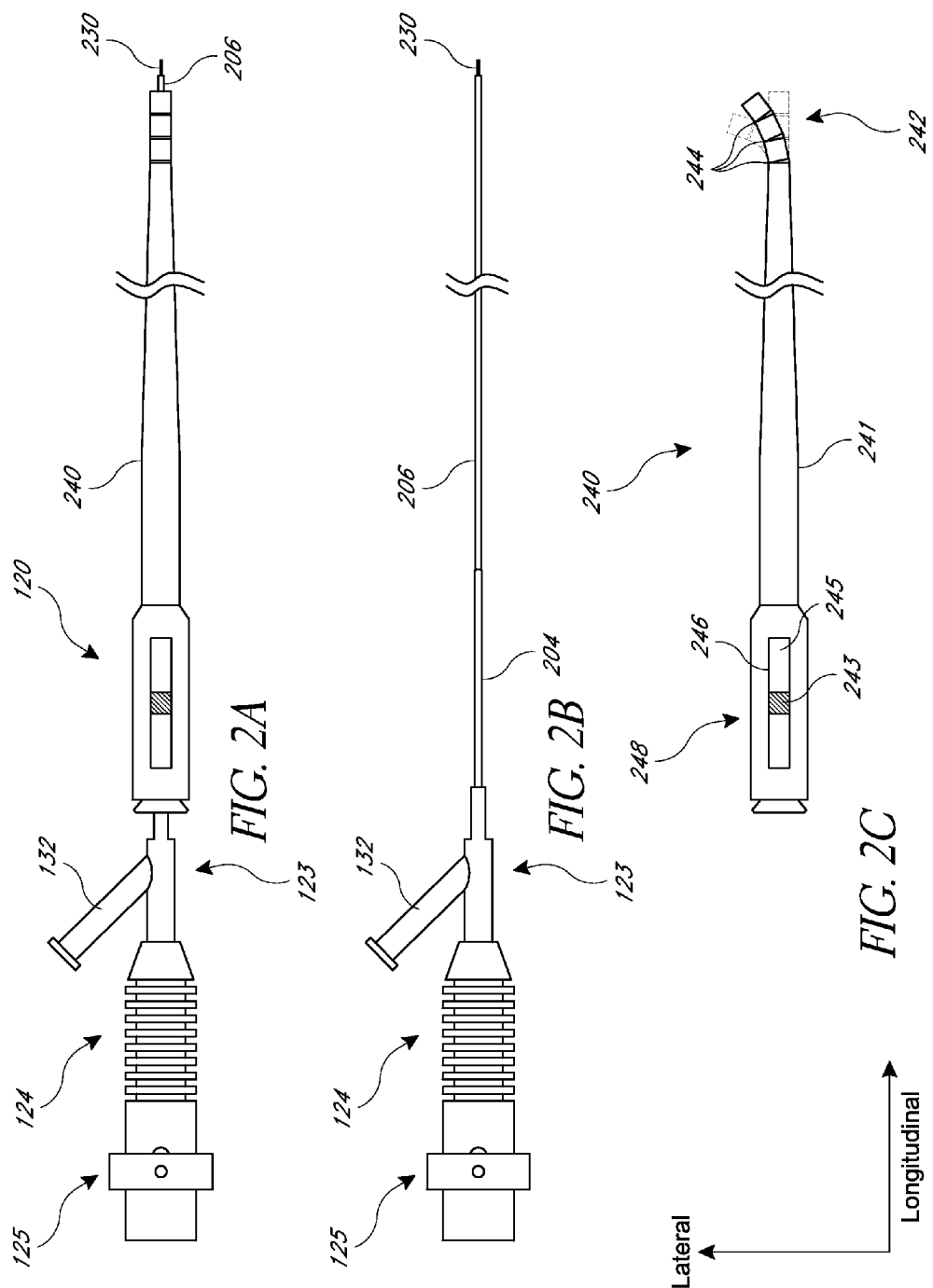

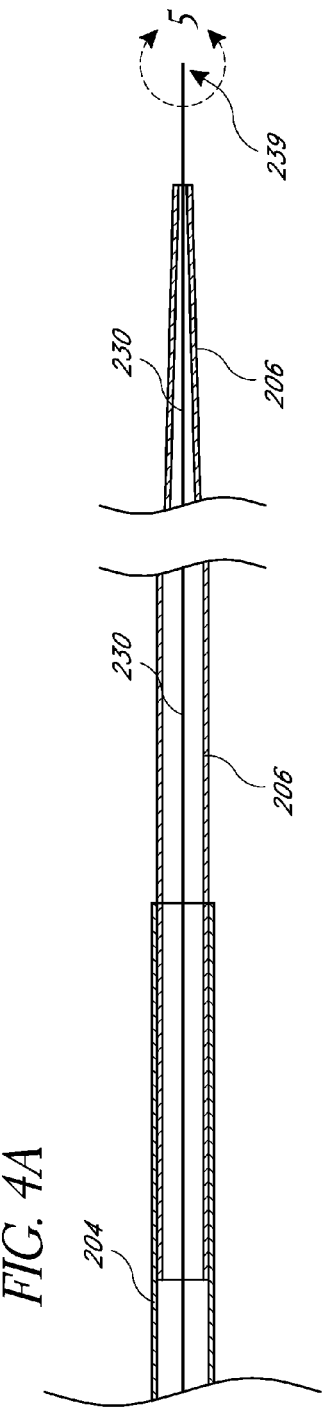
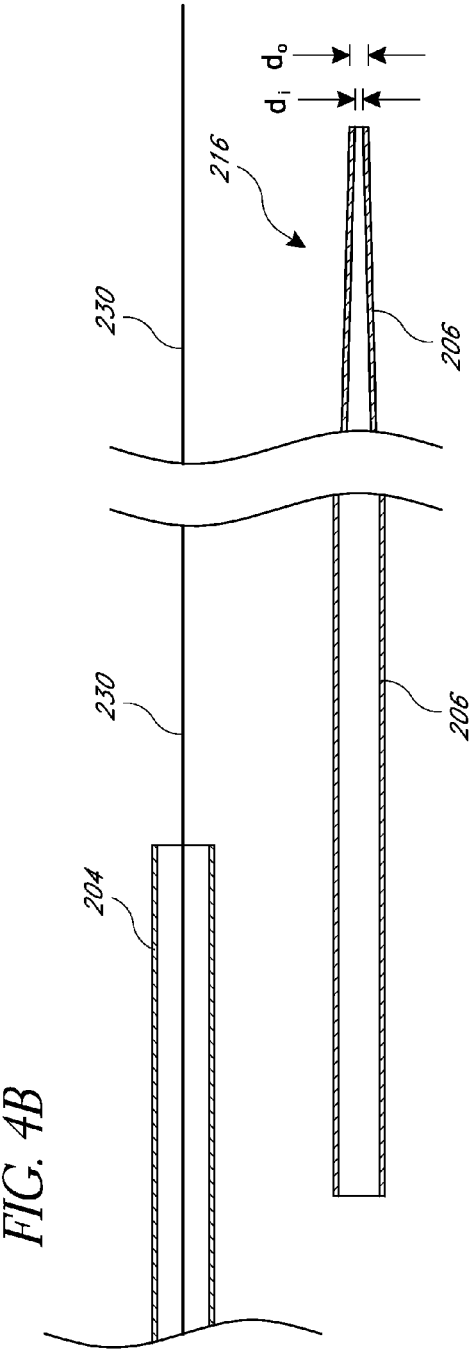
FIG. 4A
FIG. 4B

VASCULAR RE-ENTRY DEVICE

CROSS REFERENCE TO RELATED APPLICATIONS

This application is a national stage of International Application No. PCT/US2012/021766, filed Jan. 18, 2012, which is incorporated by reference in its entirety herein.

BACKGROUND OF THE INVENTION

Field of the Invention

This disclosure generally relates to a device, system, and method for treating obstructed vessels. More particularly, the disclosure relates to an ultrasound device and method for accessing the central lumen of a blood vessel from the extraluminal space of the vessel.

Description of the Related Art

There are many procedures and systems for treating vascular or venous obstructions that are occluded with atheroma, plaque, calcific material, and the like. Such obstructions are often referred to as vascular chronic total occlusions. Total occlusions can be treated, for example, by a surgical bypass procedure or a catheter-based intervention such as angioplasty.

Catheter-based intervention procedures may require the positioning of a guidewire through the occlusion. However, hard occlusive material can be difficult or almost impossible to penetrate. Often, during such procedures, the guidewire deflects from the occlusion and penetrates into an extraluminal space (i.e., subintimal or outside the vessel). The guidewire may even perforate the vessel, resulting in the distal end of the guidewire positioned outside of the vessel wall. Such perforations are very dangerous in certain circulations (e.g., in the brain and the heart). But, perforations are less risky in peripheral arterial circulations and in most of the venous system due to the muscular tissue surrounding these areas. A guidewire positioned in the extraluminal space, between layers of the vessel or outside of the vessel, must be repositioned and/or directed into the central lumen of the vessel. However, redirecting the guidewire is often difficult or impossible, even with the use of ancillary deflecting catheters or devices.

SUMMARY OF THE INVENTION

The devices and methods of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Preferred Embodiments" one will understand how the features of this invention provide several advantages over traditional procedures relating to the treatment of vascular or venous occlusions.

One aspect is an ultrasonic reentry device that includes an elongate ultrasound transmission member that has a proximal end coupled to a sonic connector and a distal end configured to penetrate a vessel wall. The device further includes a catheter body that has a distal end and at least one lumen extending longitudinally therethrough. The lumen surrounds at least a portion of the ultrasound transmission member. The device further includes a dilator removably coupled to the catheter body and surrounding at least a portion of the ultrasound transmission member. The dilator has a length sized to expose at least a portion of the distal end of the ultrasound transmission member when the ultrasound transmission member is disposed within the dilator.

Another aspect is an ultrasonic device for entering and exiting an extraluminal space of a vessel. The device includes a catheter body that has at least one lumen extending longitudinally therethrough and an elongate ultrasound transmission member extending longitudinally through the lumen. At least a portion of the ultrasound transmission member has an outer surface that tapers to a needle-like distal end. The device further includes a dilator disposed over at least a portion of the ultrasound transmission member and configured to follow the ultrasound transmission member into the extraluminal space. At least a portion of the catheter body overlaps at least a portion of the dilator. The device further includes a sheath removably disposed over at least a portion of the dilator.

Another aspect is a method of re-entry from an extraluminal space into a central lumen of a vessel. The method includes positioning an ultrasonic device having a distal end in a first position within the central lumen of the vessel and penetrating the vessel with the distal end of the ultrasonic device. The method further includes advancing the distal end to a second position within the extraluminal space of the vessel and articulating at least a portion of the distal end of the ultrasonic device. The method further includes transmitting a vibration to the distal end of the ultrasonic device and advancing the distal end to a third position different from the first position within the central lumen.

Another aspect is a method of re-entering a central lumen of a vessel from an extraluminal space of the vessel. The method includes advancing a sheath over a guidewire positioned in the extraluminal space of the vessel, removing the guidewire, and advancing an ultrasonic device having a distal end through the sheath. The method further includes articulating at least a portion of the sheath towards the central lumen of the vessel, transmitting a vibration to the distal end of the ultrasonic device, and re-entering the central lumen of the vessel with the distal end of the ultrasonic device.

Another aspect is a system configured to re-enter from an extraluminal space into a central lumen of a vessel. The system can be configured to position an ultrasonic device having a distal end in a first position within the central lumen of the vessel and to penetrate the vessel with the distal end of the ultrasonic device. The system can be further configured to advance the distal end to a second position within the extraluminal space of the vessel and to articulate at least a portion of the distal end of the ultrasonic device. The system can be further configured to transmit a vibration to the distal end of the ultrasonic device and to advance the distal end to a third position different from the first position within the central lumen.

Another aspect is a system configured to re-enter a central lumen of a vessel from an extraluminal space of the vessel. The system can be configured to advance a sheath over a guidewire positioned in the extraluminal space of the vessel, to remove the guidewire, and to advance an ultrasonic device having a distal end through the sheath. The system can be further configured to articulate at least a portion of the sheath towards the central lumen of the vessel, transmit a vibration to the distal end of the ultrasonic device, and re-enter the central lumen of the vessel with the distal end of the ultrasonic device.

BRIEF DESCRIPTION OF THE DRAWINGS

FIG. 2A is a side view of the ultrasound device shown in FIG. 1 coaxially located within a removable sheath.

FIG. 2B is a side view of the ultrasound device shown in FIG. 2A with the sheath removed.

FIG. 2C is a side view of the sheath from FIG. 2A showing an articulating distal end in dashed lines.

FIG. 4A is an enlarged view of a portion of the ultrasound device about line 4A in FIG. 3B.

FIG. 4B is a view similar to FIG. 4A except the dilator is removed from the catheter body.

DETAILED DESCRIPTION OF CERTAIN PREFERRED EMBODIMENTS

The following description and the accompanying figures describe and show the preferred embodiments as well as demonstrate several possible configurations for a re-entry device, system, and method. The illustrations are not intended to limit the disclosed aspects and features of the invention to the specified embodiments or to usage only with the illustrated device. Those of skill in the art will recognize that the disclosed aspects and features of the invention are not limited to any particular embodiment of a re-entry device, which may include one or more of the inventive aspects and features described herein.

To assist in the description of these components of the re-entry device, the following coordinate terms are used. A "longitudinal axis" is generally parallel to a portion of the re-entry device as well as parallel to the axis of a vessel through which the device can travel. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the re-entry device, and therefore is substantially synonymous with the term "longitudinal" as used herein. Also, the terms "proximal" and "distal," which are used to describe the present system, are used consistently with the description of the exemplary applications (i.e., the illustrative examples of the use applications). Thus, proximal and distal are also used in reference to the respective ends of the re-entry device.

To facilitate a complete understanding of the embodiments, the remainder of the detailed description describes the re-entry system with reference to the Figures; wherein like elements among the embodiments are referenced with like numerals throughout the following description.

Figure 1:
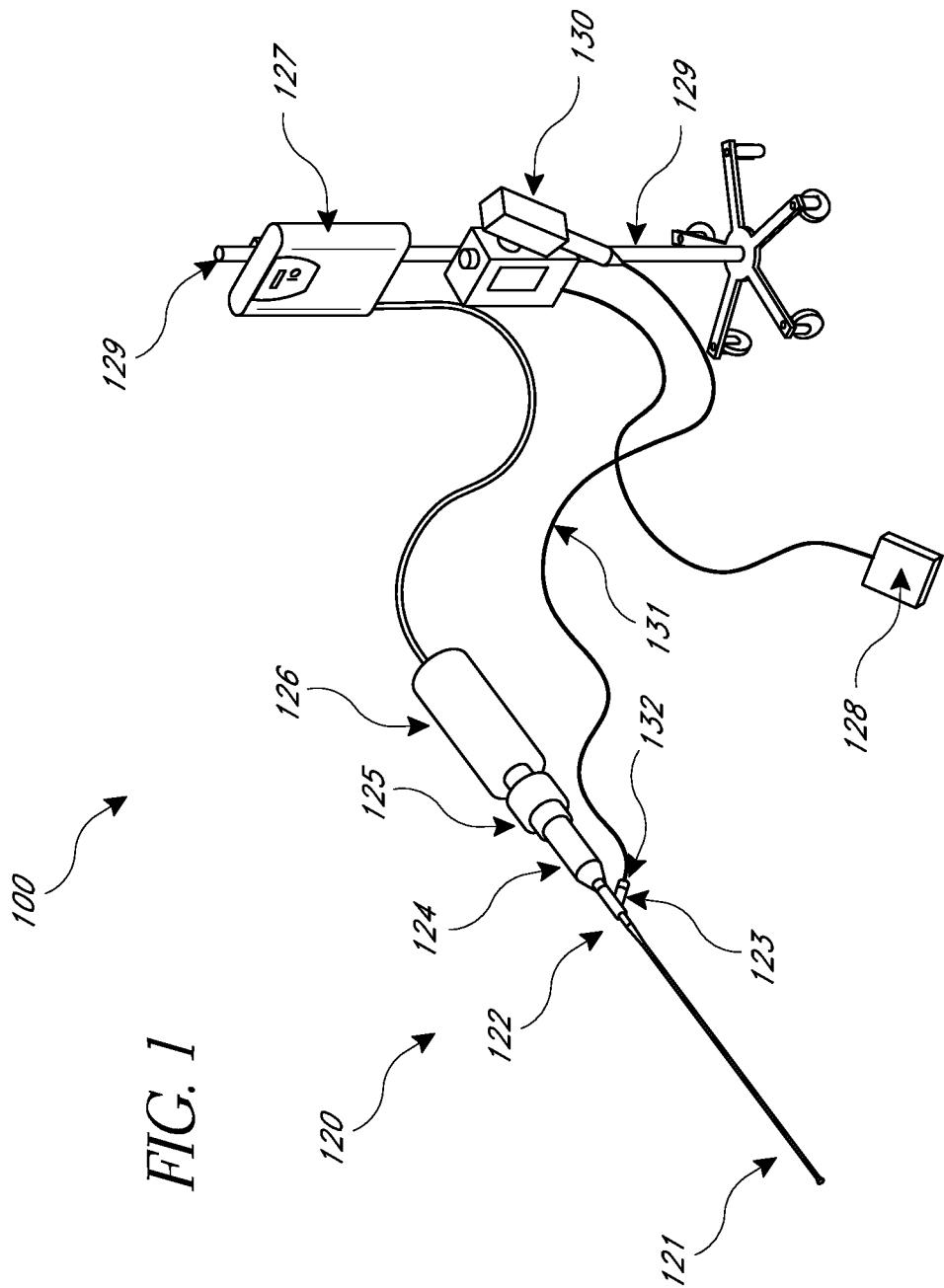
FIG. 1 is a perspective view of an ultrasound system that can be used for vascular re-entry according to a preferred embodiment of the present invention.

FIG. 1 shows an example of a perspective view of an ultrasound system 100 that can be used for vascular re-entry. The ultrasound system 100 includes an ultrasound device 120 which is releasably coupled to an ultrasound transducer 126. The ultrasound transducer 126 is electrically coupled to a signal generator 127.

The ultrasound device 120 may include an elongate body having a proximal portion 122 and a distal portion 121. The ultrasound device 120 may be an ultrasonic energy delivery member, or a catheter having at least one lumen extending longitudinally with an ultrasound transmission member extending therethrough.

The ultrasound device 120 may also include a Y-connector 123 that is operatively coupled to the ultrasound transducer 126. For example, the Y-connector 123 may be coupled to the ultrasound transducer 126 by way of a device knob 124 and a slide collar 125. The ultrasound transducer 126 may be connected to a signal generator 127, which may be coupled to a foot actuated on-off switch 128. The signal generator 127 can be supported by an IV pole 129. When the on-off switch 128 is depressed, the signal generator 127 can send an electrical signal to the ultrasound transducer 126, which converts the electrical signal to ultrasound energy. Such ultrasound energy can subsequently pass through the ultrasound device 120 and be delivered to the distal portion 121. A conventional guidewire (not shown) may be utilized in conjunction with the device 120.

The frontal portion of the Y-connector 123 may be connected to the proximal end 122 of the ultrasound device 120 using techniques that are well-known in the art. An injection pump 130 or IV bag (not shown) or syringe (not shown) may be connected, by way of an infusion tube 131, to an infusion port or sidearm 132 of the Y-connector 123. The injection pump 130 can be used to infuse coolant fluid into and/or through the device 120. Such flow of coolant fluid may be utilized to prevent overheating of the ultrasound transmission member and may serve to bathe the outer surface of the ultrasound transmission member, thereby providing for an equilibration of temperature between the coolant fluid and the ultrasound transmission member. The temperature and/or flow rate of coolant fluid may be adjusted to provide adequate cooling and/or other temperature control of the ultrasound transmission member. The irrigation fluid can include a pharmacological agent and/or microbubbles. In addition to the foregoing, the injection pump 130 or syringe may be utilized to infuse a radiographic contrast medium into the device 120 for purposes of imaging. Examples of iodinated radiographic contrast media which may be selectively infused into the ultrasonic device 120 via the injection pump 130 are commercially available as Angiovist 370 from Berlex Labs, Wayne, N.J. and Hexabrix from Malinkrodt, St. Louis, Mo.

Generally, the ultrasonic device 120 may include any suitable number of side-arms or ports for passage of a guidewire, application of suction, infusing and/or withdrawing irrigation fluid, dye and/or the like, or any other suitable ports or connections. Also, the device may be used with any suitable ultrasound transducer 126, signal generator 127, coupling device(s) and/or the like. Therefore, the exemplary embodiment shown in FIG. 1 and any following descriptions of proximal apparatus or systems for use with ultrasound devices 120 should not be interpreted to limit the scope of the present invention as defined in the appended claims.

FIG. 2A is a side view of the vascular re-entry device shown in FIG. 1 disposed within a removable sheath. The illustrated embodiment of the ultrasound device 120 includes an ultrasound transmission member 230, a dilator 206, and a sheath 240 which together form a tri-axial configuration.

As shown in FIG. 2A, the sheath 240 is removably coupled to the ultrasound device 120. The sheath 240 can be sized and shaped to fit over the catheter body 204, the dilator 206, and the ultrasound transmission member 230. The length of the sheath 240 may be selected such that a portion of the dilator 206 and/or a portion of the ultrasound transmission member 230 remain uncovered by the sheath 204 when the sheath 204 is coupled to the ultrasound device 120.

FIG. 2B is a side view of the ultrasound device 120 shown in FIG. 2A with the sheath 240 removed. As illustrated, the distal portion of the Y-connector 123 is coupled to a catheter body 204. The catheter body 204 can be coupled to the dilator 206. The ultrasound transmission member 230 can pass through the device knob 124, Y-connector 123, catheter body 204, dilator 206, and emerge at the distal end of the ultrasound device 120.

Turning to FIG. 2C, the sheath 240 can be removed from the ultrasound device 120. The sheath 240 may include a proximal handle 248, an actuating distal portion 242, and at least one lumen extending therethrough. The handle 248 may include a mechanism for actuating 246 the distal portion 242. The mechanism 246 may be a member 243 which slides within a channel 245. The member 243 may be coupled to a puller wire (not shown) such that when the member 243 is moved in a longitudinal direction away from the distal portion 242, the puller wire is moved in the same direction causing the distal portion 242 to deflect. In some embodiments, the distal portion 242 deflects up to about 90° from the longitudinal axis. In other embodiments, the distal portion 242 deflects greater than 90°. An advantage of an articulating distal portion 242 over a pre-shaped or curved catheter is the distal portion 242 remains straight when propagating though a vessel and/or extraluminal space, thus reducing trauma to the vessel. Furthermore, the actuating distal portion 242 may allow for added control and accuracy because the amount of deflection can be controlled and/or selected. Sheath 240 may be similar to commercially available sheaths such as, for example, the Bard® Channel™ Steerable Sheath (available from C. R. Bard, Inc., Lowell, Mass.), the CPS Venture® Wire Control Catheter (available from St. Jude Medical, Inc., St. Paul, Minn.), and the Morph® Vascular Access Catheter (available from BioCardia, Inc., San Carlos, Calif.) or other similar such products.

The handle 248 may be coupled with a shaft 241 having at least one lumen extending therethrough. In some embodiments, the shaft 241 is generally tubular in shape and may be constructed to resist snaking when pushed. A stiff shaft construction can prevent snaking when the puller wire is actuated causing the distal portion 242 to deflect. The sheath 240 may be any suitable length, for example, in the range of about 70-150 mm and any suitable diameter, for example, in the range of about 1.5-2.5 mm in order to be positioned though a vascular or venous system.

In some embodiments, the distal portion 242 includes one or more radiopaque markers 244. In one embodiment, the distal portion 242 is made of a radiopaque polymer or similar materials known in the art. The radiopaque materials can increase visibility under fluoroscopy and facilitate the correct positioning of the device. In another embodiment, intravascular ultrasound or other imaging modalities may be employed. Alternate imaging techniques may include Optical Coherence Tomography (OCT) and/or magnetic fields (Stereotaxis Inc.) to further facilitate orientation of the distal portion 242 towards the central lumen of a vessel and further aid in the re-entry procedure.

Figure 3A:
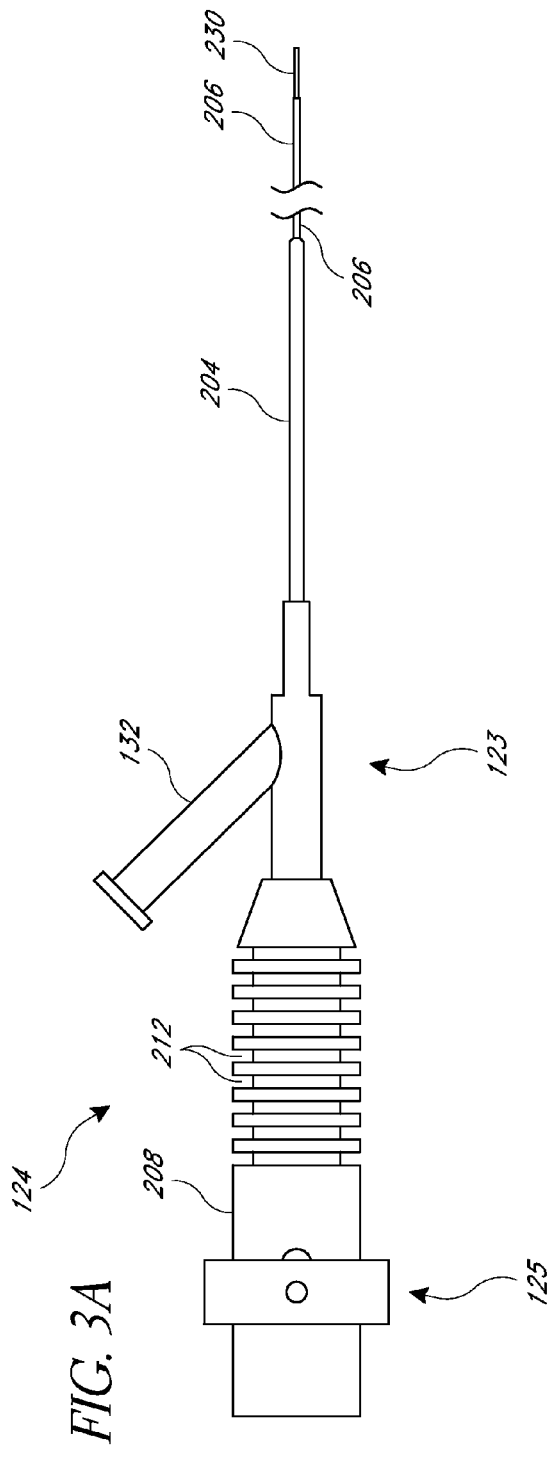
FIG. 3A is an enlarged side view of the ultrasound device as shown in FIG. 2B.

FIG. 3A is an enlarged side view of the ultrasound device 120 as shown in FIG. 2B. In the illustrated embodiment, the device knob 124 includes a proximal housing 208. The housing 208 may include one or more surface features 212 for increasing the outer surface area of housing 208. Increased surface area can enhance the ability of housing 208 to dissipate heat generated by ultrasound transmission member 230. Surface features 212 may be of any suitable size or shape and can include, for example, ridges, jags, undulations, grooves or the like. Any suitable number of surface features 212 may be used. Additionally, the housing 208 may be made of one or more heat dissipating materials, such as aluminum, stainless steel, any other conductive metal(s), or any suitable non-metallic conductive material.

The catheter body 204 may be a generally flexible, tubular, elongate member, having any suitable diameter and length for reaching a vascular occlusion. Some embodiments, for example, the catheter body 204 has a length in the range of about 100-200 cm. In one embodiment, the catheter body 204 has an outer diameter in the range of about 0.5-5.0 mm. In other embodiments, for use in relatively small vessels for example, the catheter body 204 may have an outer diameter in the range of about 0.25-2.5 mm. However, any other suitable length or diameter may be used without departing from the scope of the present invention. Examples of catheter bodies similar to those which may be used in the present invention are described in U.S. Pat. Nos. 5,267,954 and 5,989,208, which are herein incorporated by reference in their entireties. The catheter body 204 can insulate the ultrasound transmission member 230 and prevent an operator's hands from contacting the ultrasound transmission member 230 during use of the device.

Figure 3B:
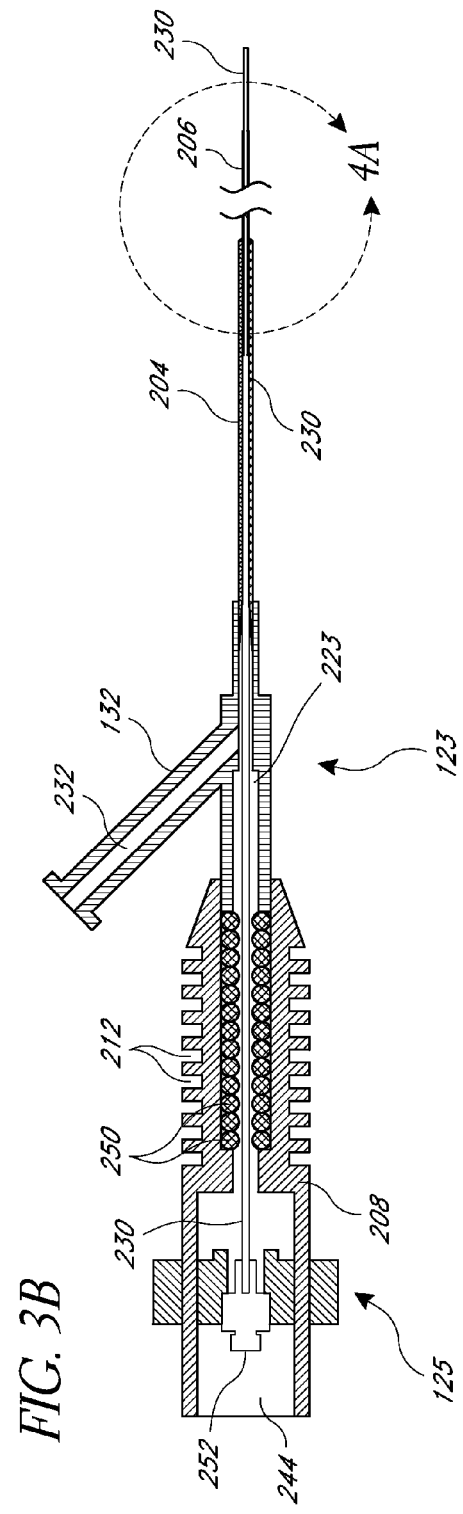
FIG. 3B is a cross-sectional view of the ultrasound device as shown in FIG. 3A.

FIG. 3B shows a cross-sectional view of the ultrasound device 120. As depicted, the housing 208 can include an inner cavity 244. Disposed within the cavity 244 is a sonic connector 252. The ultrasound transmission member 230 extends in a distal direction from the sonic connector 252 and through the cavity 244.

The inner cavity 244 may include one or more vibration absorption members 250. The vibration absorption members 250 can increase the ease of use by decreasing vibrations transmitted from the ultrasound transmission member 230 through the housing 208. The sonic connector 252 can facilitate the coupling of the ultrasound transmission member 230 to an ultrasound transducer device 126. The ultrasound transmission member 230 may extend distally from the sonic connector 252, through the inner cavity 244, Y-connector 216, catheter body 204, and dilator 206.

Continuing with FIG. 3B, the sidearm 132 may include a lumen 232 in fluid communication with a lumen 223 in the Y-connector 123. The lumen 223 in the Y-connector 123 can be in fluid communication with a lumen extending through the catheter body 204. Thus, fluid introduced into the sidearm 132 may flow into and through the catheter body 204 and contact the ultrasound transmission member 230. The fluid may flow out of the catheter body 204 through apertures in the distal portions (not shown) or through any other suitable apertures or openings, such as apertures located in the catheter body 204 itself.

Any suitable fluid may be passed through the sidearm 132 and catheter body 204. Suitable fluids include, for example, refrigerated fluids, lubricious fluids, super-saturated saline or contrast/saline mixtures, or the like. Cooling and/or lubricating the ultrasound transmission member 230 may reduce friction and/or wear and tear of the ultrasound transmission member 230, thus prolonging the ultrasound transmission member's useful life and enhancing overall performance.

In some embodiments, the ultrasound transmission member 230, wire, or wave guide extends longitudinally through a lumen of the catheter body 204. Ultrasonic energy can travel through the ultrasound transmission member 230 from an ultrasound transducer 126 connected to the proximal end of housing 208 to the distal portion of the device. The ultrasound transmission member 230 may operate at frequencies between about 10 Hz to about 20 MHz. In one embodiment, the frequency of vibration is 20 kHz. The ultrasound transmission member 230 may operate in continuous mode, pulse mode, or combination of both.

The ultrasound transmission member 230 may be formed of any material capable of effectively transmitting ultrasonic energy from the ultrasound transducer to the distal end of the ultrasound transmission member 230. These materials include, but are not limited to, metals such as pure titanium or aluminum, or titanium or aluminum alloys, such as NiTi. The ultrasound transmission member 230 may include one or more tapered regions and/or steps. The tapered regions and steps may increase and/or decrease in width or diameter along the length of the ultrasound transmission member 230 in the distal direction. In one embodiment, the ultrasound transmission member 230 includes at least one portion tapered in a direction extending distally from the proximal end. In another embodiment, the ultrasound transmission member 230 is continuously tapered in a direction extending distally from the proximal end. In one embodiment, the ultrasound transmission member 230 tapers in diameter from about 800 μm proximally, to about 200 μm distally.

Additional details of ultrasound systems and devices that include ultrasound transmission members (and their distal tips), ultra-sound transducers, sonic connectors and their connections to ultrasound devices are disclosed in U.S. Pat. Nos. 6,007,514; 6,427,118; 6,702,748; 6,855,123; 6,942,620; 6,942,677; 7,137,963; 7,220,233; 7,297,131; 7,335,180; 7,393,338; 7,540,852, 7,604,608 and in U.S. Pat. Pub. Nos. 2008/0108937, 2008/0287804, 2010/0317973, the disclosures of which are hereby incorporated by reference in their entireties.

Continuing with FIG. 3B, the Y-connector 123 can be coupled to the catheter body 204. The catheter body 204 can be coupled to the removable dilator 206. The Y-connector 123 can be coupled to the catheter body 204 by any coupling manner well known in the art and in some embodiments is fixably attached. Similarly, the removable dilator 206 can be coupled to the catheter body 204 in any manner well known in the art. In some embodiments, a separate coupling structure is used.

In some embodiments, as shown for example in FIGS. 4A and 4B, the removable dilator 206 is coupled to the catheter body 204 such that the catheter body 204 overlaps at least a portion of the dilator 206. As illustrated, a proximal portion of the dilator 206 is sized to fit within a distal portion of the catheter body 204. In other words, the dilator 206 can be placed around the ultrasound transmission member 230 and fit within the catheter body 208.

In some embodiments, an outer surface of the dilator 206 contacts an inner surface of the catheter body 204. Friction between the two surfaces can secure the dilator 206 in place. The length of the dilator 206 may be selected so that at least a portion of the ultrasound transmission member 230 is exposed at the distal end. The total length of the dilator 206 can be selected, for example, such that about 5 mm of the distal portion of the ultrasound transmission member 230 is exposed when a proximal portion of the dilator 206 is fit snugly within the distal portion of the catheter body 204.

The dilator 206 may be a thin walled tubular member and constructed such that the dilator 206 is resistant to bending or kinking when pushed. The dilator 206 may be formed with any suitable material well known in the art, including but not limited to flat-ribbon braided polyamide, or may comprise a hypotube catheter shaft of stainless steel, titanium, NiTi, or similar metal/alloy. In one embodiment, at least a portion of the dilator 206 is tapered in a direction extending distally from the proximal end. In another embodiment, the dilator 206 is continuously tapered in a direction extending distally from the proximal end.

Turning to FIG. 4B, a distal portion of the dilator 206 may have a similar profile to the ultrasound transmission member 230 such that the distal portion of the dilator 206 is sized to facilitate the following of the ultrasound transmission member 230 into the extraluminal space. In use, the dilator 206 can serve as a transition member between the relatively small diameter of the ultrasound transmission member 230 and the relatively larger diameter of the sheath 240. For example, the dilator 206 can follow the ultrasound transmission member 230 into the extraluminal space and the sheath 240 can then follow the dilator 206 into the extraluminal space as well. In one embodiment, the distal portion of the dilator 206 has an inner diameter $d_i$ and outer diameter $d_o$ in the range of about 500-250 μm. In one embodiment, the inner diameter $d_i$ is about 380 μm and the outer diameter $d_o$ is about 480 μm.

Figure 5B:
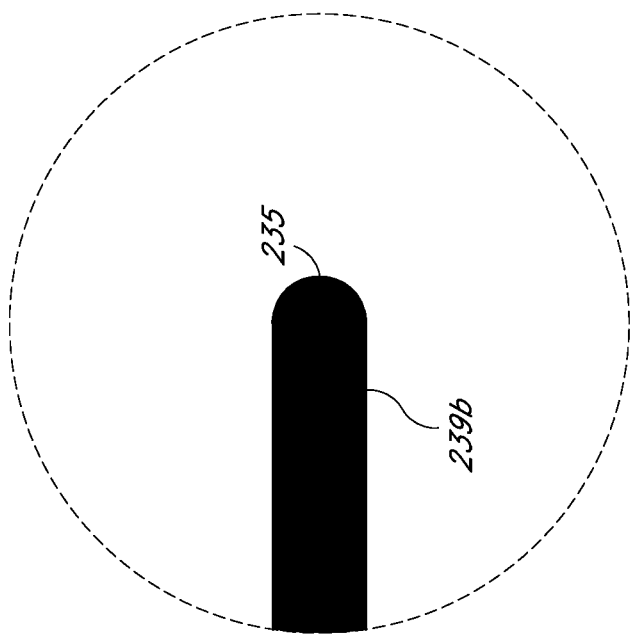
FIG. 5B is an enlarged view of another embodiment of the distal end of the ultrasound device about line 5 in FIG. 4A.
Figure 5A:
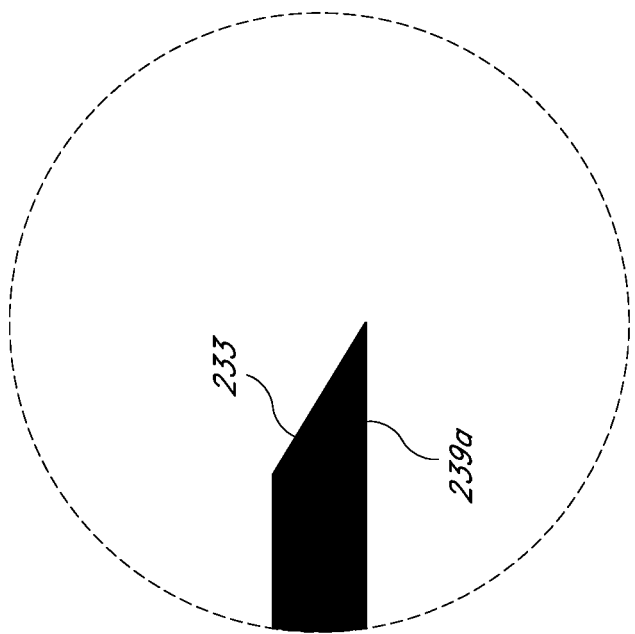
FIG. 5A is an enlarged view of an embodiment of a distal end of the ultrasound device about line 5 in FIG. 4A.

FIGS. 5A and 5B show enlarged side views of exemplary embodiments of the distal tip 239 of the ultrasound transmission member 230. In some embodiments, the distal tip 239 is integral to the ultrasound transmission member 230 and is not formed by a separate tip structure or component attached to the ultrasound transmission member 230. Rather, in these embodiments, the distal tip 239 is formed by shaping the distal end of the ultrasound transmission member 230. A sharpened distal end facilitates penetration into blood vessel materials. The lack of an affixed tip structure which often includes a larger diameter allows for greater power intensity to be transmitted to the distal tip 239 of ultrasound transmission member 230. FIG. 5A shows a distal tip 239*a* with a chiseled end, having a beveled edge 233. FIG. 5A shows a distal tip 239*b* with a rounded edge 235. Other similar constructions may also be implemented. For example, in one embodiment, the distal tip of ultrasound transmission member 239 has a conical shape.

A Total Occlusion ("TO") can be defined as an artery or vein that has been completely occluded. An acute TO is usually associated with a sudden blockage, resulting in no blood flow to and from surrounding tissue, and is potentially life threatening. In contrast, Chronic Total Occlusions ("CTO") are blockages that have formed for at least thirty days and are less life-threatening. In such cases, the areas around the CTO tend to develop collateral blood supply.

Figure 6:
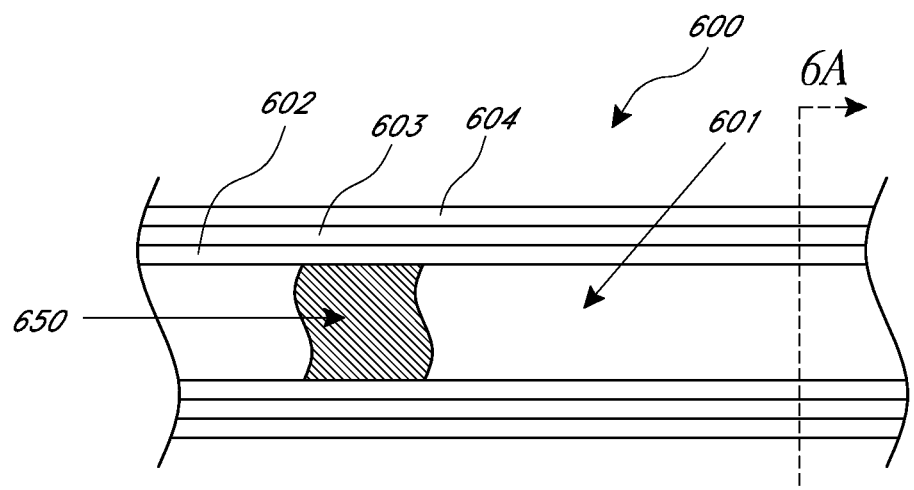
FIG. 6 shows a longitudinal cross-sectional view of an artery having a total occlusion (TO) or chronic total occlusion (CTO).

FIG. 6 illustrates a longitudinal cross-sectional view of an artery 600 having a total occlusion 650. The total occlusion 650 usually consists of atheroma, thrombus, plaque, calcific material, or combinations of thereof. For illustrative purposes, an arterial CTO 650 is shown in connection with the device and method described with respect to FIGS. 7-13. However, all the devices and methods described herein can also apply to CTOs within veins. Further, although the ultrasonic device will be shown and described for use in and about an artery, the device may also be used in other blood vessels including veins and capillaries or in other tubular channels, for example channels of the lymphatic system. As illustrated in FIG. 6, the arterial occlusion 650 occupies the entire diameter of the lumen, thus blocking blood flow. It is desirable to open such an occlusion, restoring blood flow through affected areas, and thus improving blood supply and heart function.

Figure 6A:
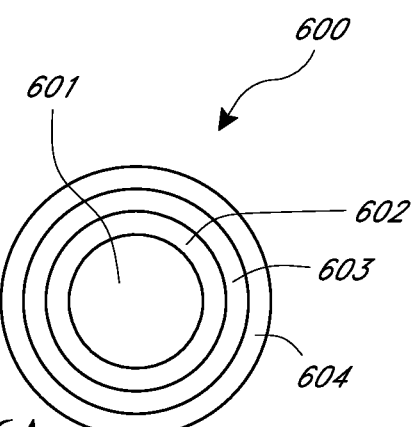
FIG. 6A shows a lateral cross-sectional view through the artery of FIG. 6 taken at line 6A-6A.

FIG. 6A illustrates a cross section of the artery 600 about the line 6A-6A as viewed in a direction distal to the occlusion. The artery has a central lumen 601 and arterial wall with three layers: intima 602, intermedia 603 and adventitia 604. All three layers consist of elastic tissue, smooth muscle and connecting tissue (collagen). The tissue of the arterial wall is often called a subintimal space. The area outside the adventitia 604, an external layer of the artery, is called a space outside of the vessel. Both areas, subintimal space and outside the vessel space, are referred to collectively herein as "extraluminal space."

Figure 7:
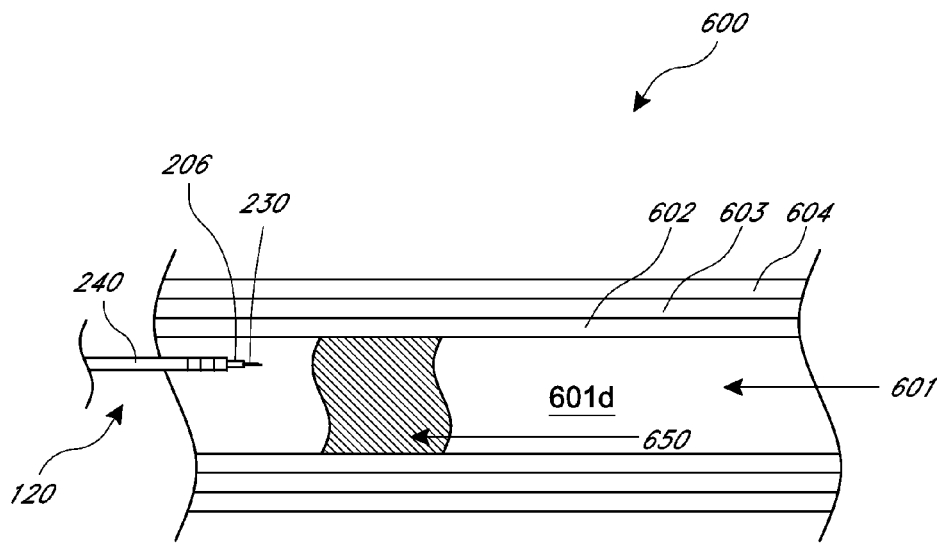
FIGS. 7-13 show an exemplary series of steps to bypass the CTO using the ultrasound device disclosed herein.

FIGS. 7-13 illustrate the steps of an exemplary use of the ultrasonic device 120 in a vascular re-entry procedure. As shown in FIG. 7 the ultrasonic device 120 can be positioned in the vessel 600 and advanced until the device 120 encounters the occlusion 650. In the illustrated embodiment, the ultrasonic device 120 includes an ultrasound transmission member 230 disposed within a dilator 206. The dilator 206 and ultrasound transmission member 230 are further disposed within the sheath 240. The sheath 240 includes an articulating distal portion.

Figure 8:
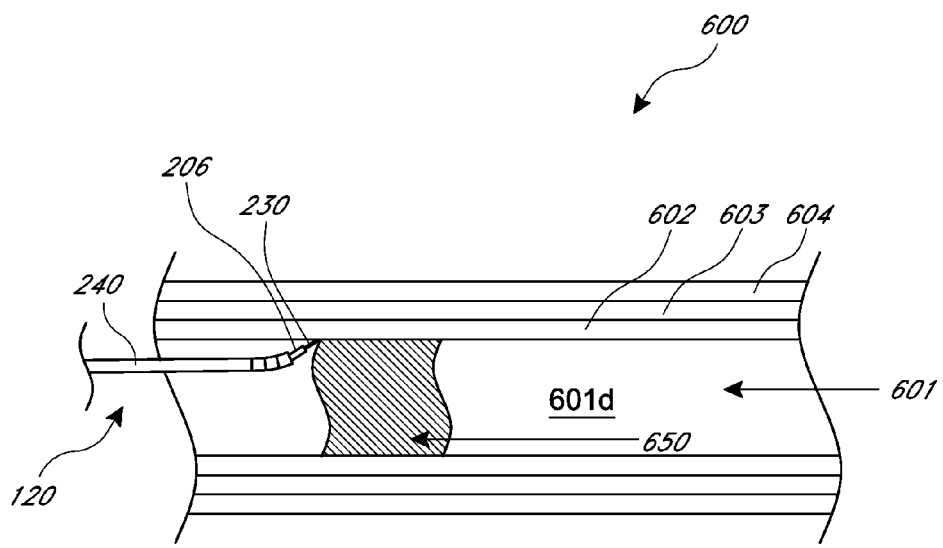

Sometimes, the ultrasonic device 120 can be successfully advanced through the occlusion 650 and positioned in the central lumen 601d of the vessel 600, distal to the occlusion. However, as shown in FIG. 8, the ultrasonic device 120 may deflect away from the occlusion 650 and toward the wall of the vessel. In FIG. 8, the ultrasonic device 120 is shown as deflecting laterally, towards the vessel wall.

Figure 9:
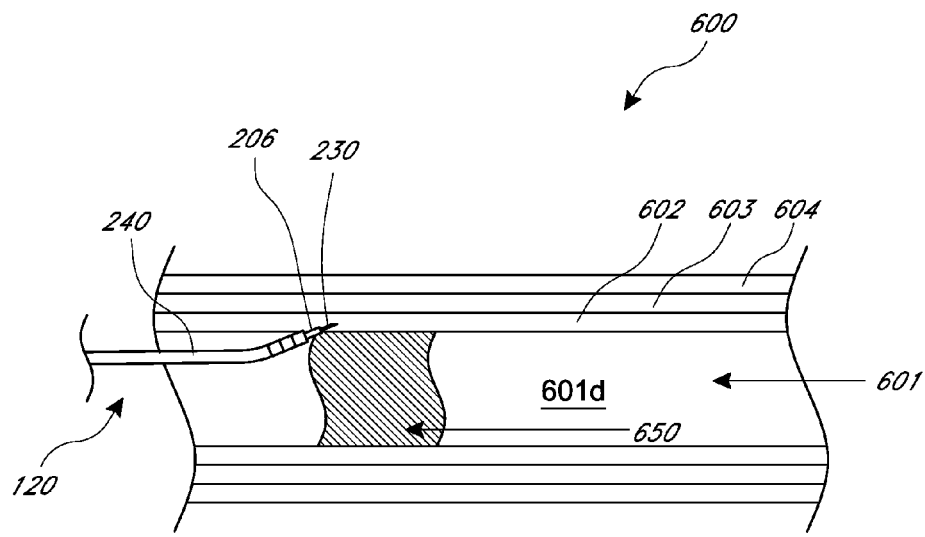

With reference to FIG. 9, the ultrasonic device 120 is advanced further so as to penetrate the intima layer 602 of the vessel 600. A sharp tipped 239 ultrasound transmission member 230 can allow for easier penetration into the intima layer 602. As the ultrasonic device 120 is advanced further, the low-profile dilator 206 follows the ultrasound transmission member 230 into the intima layer 602 as well.

Figure 10:
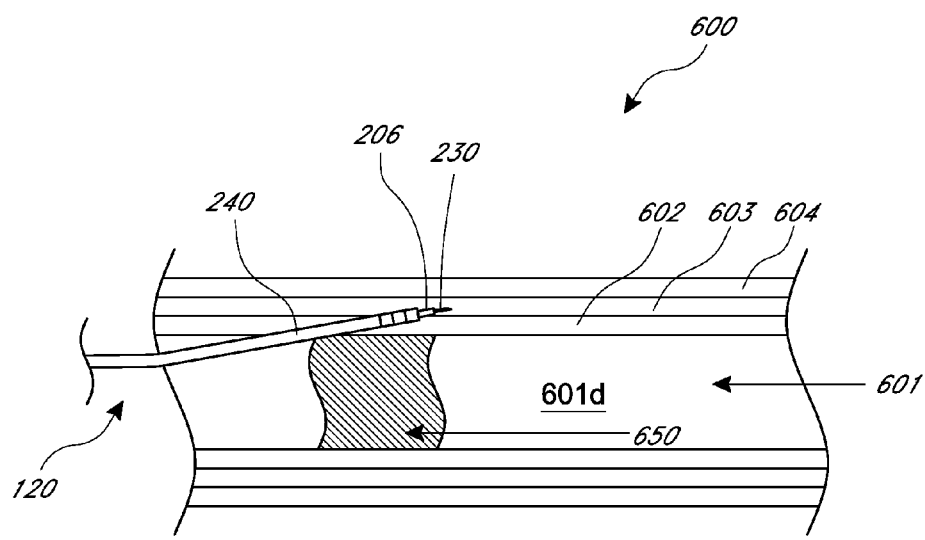

Continuing to FIG. 10, the ultrasonic device 120 is advanced further within the extraluminal space of the vessel 600. As illustrated, the sheath 240 follows the dilator 206 into the intima layer 602 such that the distal portion of the ultrasonic device 120 is positioned between the intima layer 602 and the intermedia layer 603. The ultrasonic device 120 may also be advanced into the adventitia 604 layer or even to areas outside the vessel 600. In one embodiment, the ultrasonic device 120 is advanced within the subintimal space until it passes the occlusion 650.

Vessel trauma can be minimized if the distance that the ultrasonic device 120 travels through the subintimal space is minimized. Thus, it is desirable that the path length of the ultrasonic device 120 through the subintimal space is as short as possible. In some embodiments, the ultrasonic device 120 is advanced to just beyond the proximal end of the occlusion 650. Often, when occlusions are long and there is evidence of softer occlusion composition, the proximal advancement of the ultrasonic device 120 should be limited as much as possible. Thus, if possible, re-entry within the occlusion 650 should be considered as well to minimize the length of the subintimal space in which the ultrasonic device 120 will occupy.

With other similar devices, re-entry from the subintimal or extraluminal space into the central distal lumen 601d may be difficult. For example, a conventional guidewire may be unable to re-enter into the distal central lumen 601d due to the muscular vessel structure which may prevent the relative soft guidewire from puncturing the vessel wall. A directing catheter disposed over the guidewire may also not provide sufficient support for the guidewire to puncture the vessel wall. Traditional directing catheters are often pre-shaped, causing added damage to the vessel wall.

Figure 11:
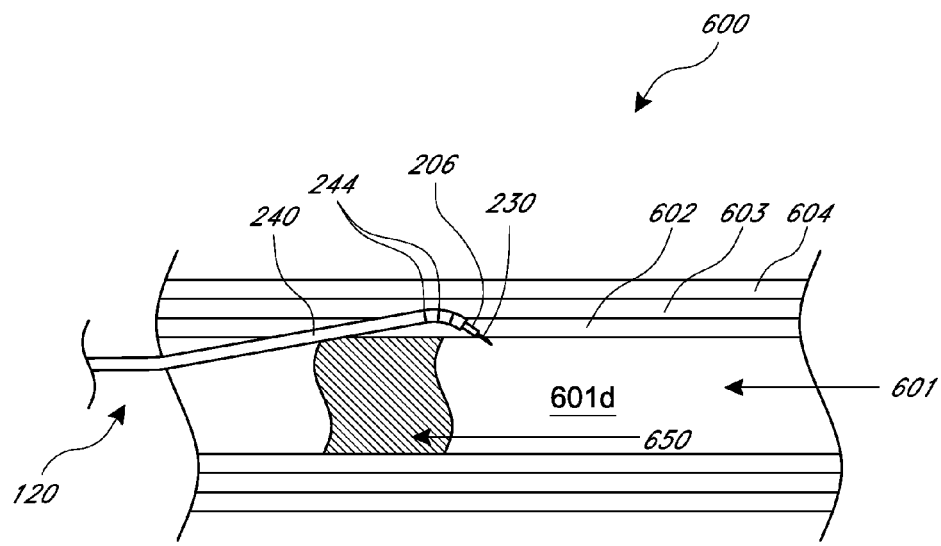

FIG. 11 shows a distal portion of the ultrasonic device 120 positioned within the subintimal space beyond the occlusion 650. In one embodiment, the position of the sheath 240 is determined at least in part by visualizing the radiopaque markers 244 with fluoroscopy techniques. The ultrasonic device 120 can be rotated and/or advanced as desired based at least in part on the known location of the radiopaque markers 244. Once the ultrasonic device 120 is placed in a desired position, the sheath 240 can be actuated such that the distal portion of the sheath 240 deflects in a direction towards the distal central lumen 601d. The precise amount of deflection can be selected and/or varied during the procedure by the device operator.

In order to determine the precise position and orientation of the ultrasonic device 120, extensive flouroscopical visualization from several X-ray machine angles may be required. Such visualization may be needed during positioning to assure that the distal portion of the device is directed towards the distal central lumen 601d. Use of endovascular ultrasound or other visualization devices, either in arteries or in adjacent veins, may also facilitate directing the distal portion of the ultrasonic device 120 towards the distal central lumen 601d.

According to one embodiment, when it is confirmed that the distal portion of the ultrasonic device 120 is directed towards the distal central lumen 601d, ultrasonic energy is transmitted to the distal portion of the ultrasound transmission member 230. The ultrasonic device 120 is then slowly advanced through the subintimal space to puncture the vessel wall. The ultrasonic device 120 can then be advanced into the distal central lumen 601d. The delivery of ultrasonic energy may then be reduced or stopped.

Ultrasonic energy, with its cavitational and/or thermal effects, may be helpful in ablating or penetrating, perforating, or piercing the vessel 600 and facilitate re-entry into the distal central lumen 601d. Vibrational devices with longitudinal or transverse vibrational forces, rotational devices, or other heat generating devices such as radio frequency or microwave devices may be used to facilitate re-entry into the distal central lumen 601d. As such, in other embodiments, the ultrasonic device 120 may include other vibrational devices, rotational devices, cutting devices, radio frequency devices, laser devices, microwave devices, puncture devices, and the like.

Figure 12:
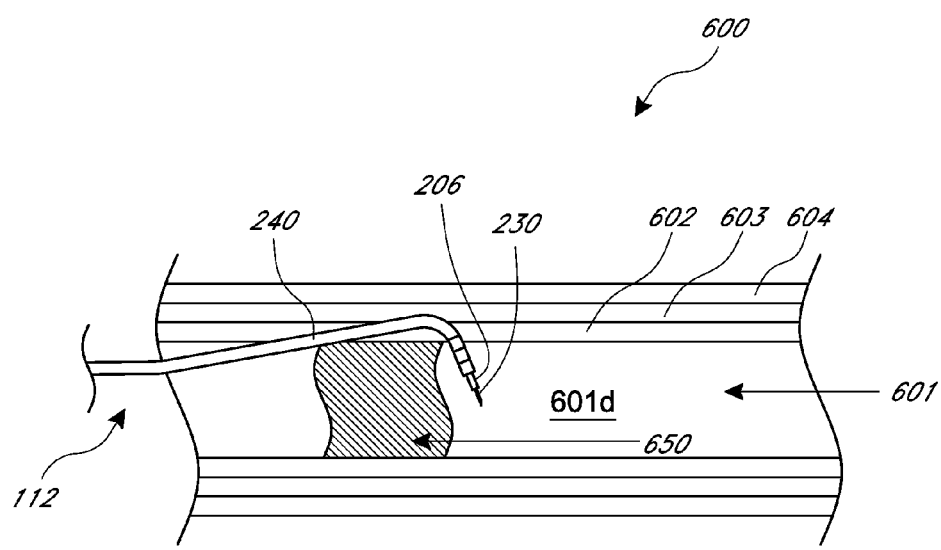

FIG. 12 illustrates a distal portion of the ultrasonic device 120 positioned in the distal central lumen 601d beyond the occlusion 650. In some embodiments, the portion of the ultrasound transmission member 230 exposed (i.e. not covered by the dilator 240 and/or sheath 206) is minimized in order to reduce the potential for piercing the opposite wall of the vessel 600.

Figure 13:
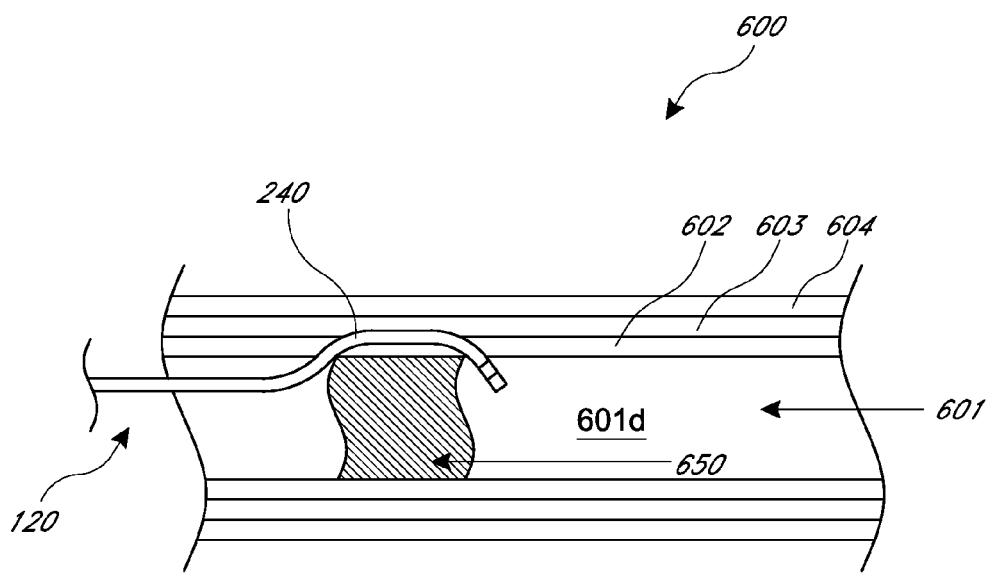

In the embodiment shown in FIG. 13, once at least a portion of the sheath 240 is positioned distal to the occlusion 650 and within the distal central lumen 601d, the ultrasound transmission member 230 and the dilator 206 can be removed from the sheath 240. An adjunctive angioplasty such as balloon angioplasty and/or stenting can then be inserted into the sheath 240. The sheath 240 can then be removed and the adjunctive angioplasty can be deployed, completing the procedure according to one embodiment.

Figure 14:
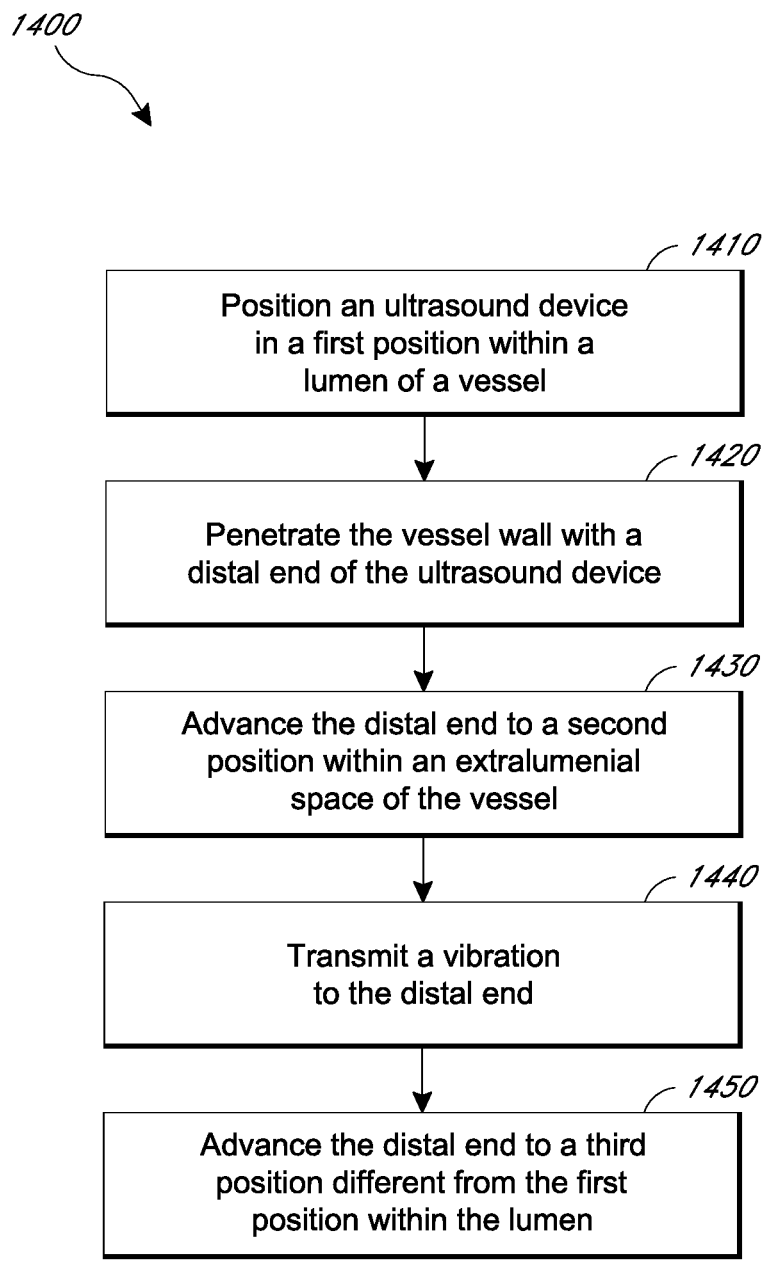
FIG. 14 is a flow diagram illustrating a method of bypassing the CTO by re-entering the artery from an extraluminal space.

FIG. 14 is a flow diagram illustrating a method of re-entry from an extraluminal space into a lumen of a vessel. The method 1400 begins at block 1410 by positioning an ultrasound device 120 in a first position within a lumen of a vessel. The first position may be proximal to a vessel blockage. The method continues at block 1420 by penetrating the vessel wall with a distal end of the ultrasound device 120. At least a portion of the distal end preferably articulates or bends. In some embodiments, the ultrasound transmission member includes a sharpened distal end configured to facilitate the ultrasound device 120 penetrating the vessel wall. The method continues at block 1430 by advancing the distal end of the ultrasound device to a second position. The second position may be within an extraluminal space of the vessel, for example, in a space outside of the lumen of the vessel, or within the vessel wall. In some embodiments, at least a portion of the distal end is articulated to bend in a direction towards or away from the vessel wall.

The method 1400 continues at block 1440 by transmitting a vibration to the distal end. The vibration may be in the form of an ultrasonic vibration transmitted from a proximal end of the ultrasonic device to the distal end. The method 1400 can end at block 1450 by advancing the distal end to a third position different from the first position within the lumen. The third position may be at a position distal to the vessel blockage. The ultrasound device 120 may include an outer lumen surrounding an ultrasound transmission member 230. In some embodiments the method continues by removing the ultrasound transmission member 230 from the lumen and replacing it with a stent or balloon catheter or the like.

FIGS. 15-25 show another exemplary series of steps to repair an initially unsuccessful bypass procedure using the ultrasound device 120 disclosed herein. As discussed above, an occluded vessel can be treated at least in part by positioning a guidewire through the occlusion. For some methods of bypassing an occlusion or CTO, the procedure initially begins with the medical provider feeding a conventional guidewire through the vasculature and adjacent to the CTO. The medical provider may then press the guidewire firmly against the CTO in an attempt to penetrate the CTO unaided by the ultrasound device 120. In such cases, the guidewire may successfully penetrate the CTO or be deflected away from the CTO and into the wall of the vessel. In some cases the deflected guidewire punctures the vessel wall and enters the subintimal space. As set forth below, one of the many medical uses for the ultrasound device 120 is to reposition such a guidewire back within the true lumen of the vessel.

Figure 15:
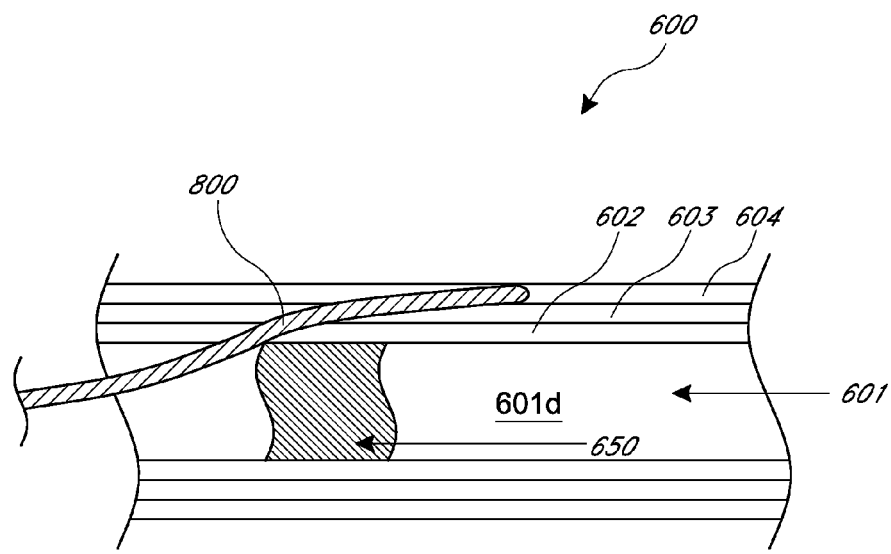
FIGS. 15-25 show another exemplary series of steps to repair an unsuccessful bypass procedure by repositioning a conventional guidewire using the ultrasound device disclosed herein.

FIG. 15 illustrates a traditional guidewire 800 that has deflected away from an occlusion 650, toward the wall of the vessel, and into the subintimal space. The tri-axial ultrasound device 120 can be used in a method to reposition the guidewire 800 in a desired position as described below.

Figure 16:
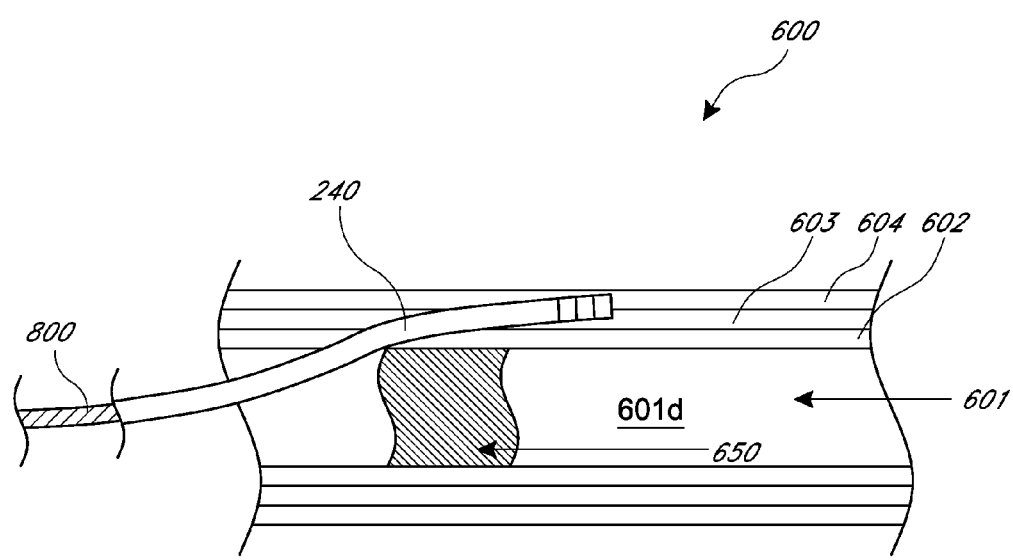

In some embodiments, the bailout method begins as is illustrated in FIG. 16 with a sheath 240 being advanced over the guidewire 800 and into the subintimal space of the vessel. The sheath 240 may include radiopaque markers 244 to help determine the precise position and orientation of the sheath 240. The sheath 240 can include an articulating distal end as discussed above.

Figure 17:
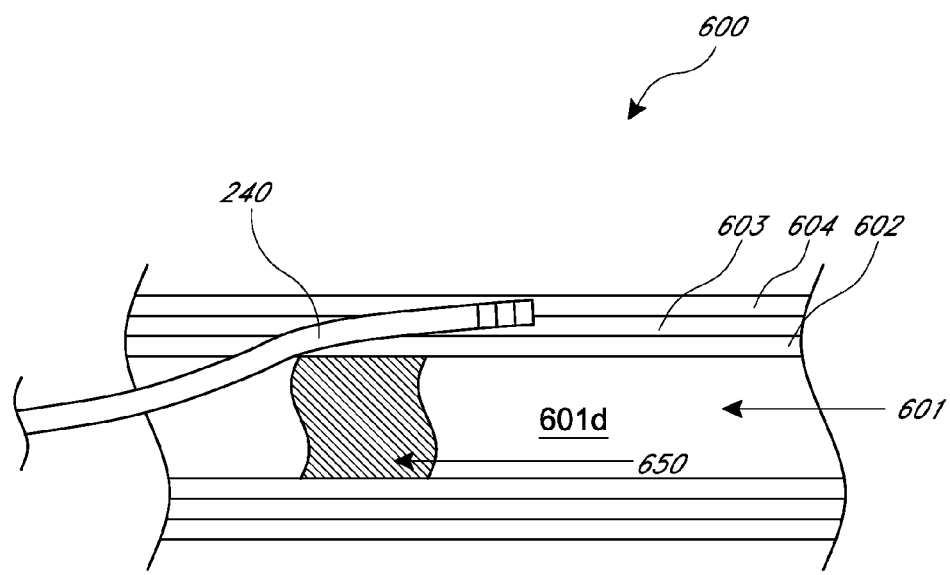

The method continues in FIG. 17 by removing the guidewire 800 from the sheath after the sheath 240 has been advanced over the guidewire 800. In this way, at least a portion of the sheath 240 remains at least partially within the subintimal space. The positioning of the sheath 240 can be determined, for example, by visualizing the radiopaque markers 244.

Figure 18:
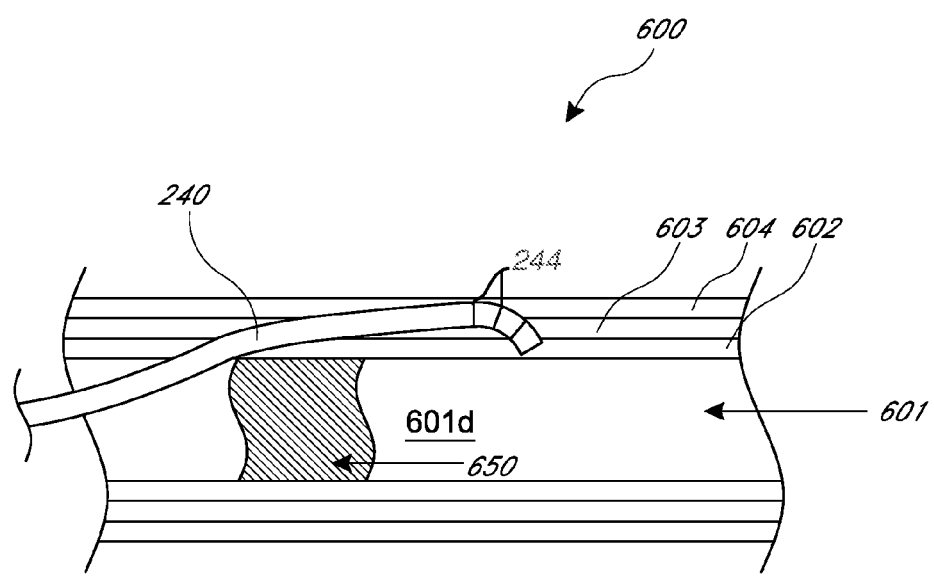

The articulating distal end of the sheath 240 can then be actuated such that a distal portion of the sheath 240 deflects in a direction toward the distal central lumen 601*d* of the vessel as shown in FIG. 18. FIG. 18 illustrates an embodiment in which the sheath 240 is articulated with the guidewire 800 removed. However, the sheath 240 can be articulated before the guidewire 800 is removed as well. The sheath 240 can also be articulated before or after other devices or lumens have been inserted into the sheath 240.

Figure 19:
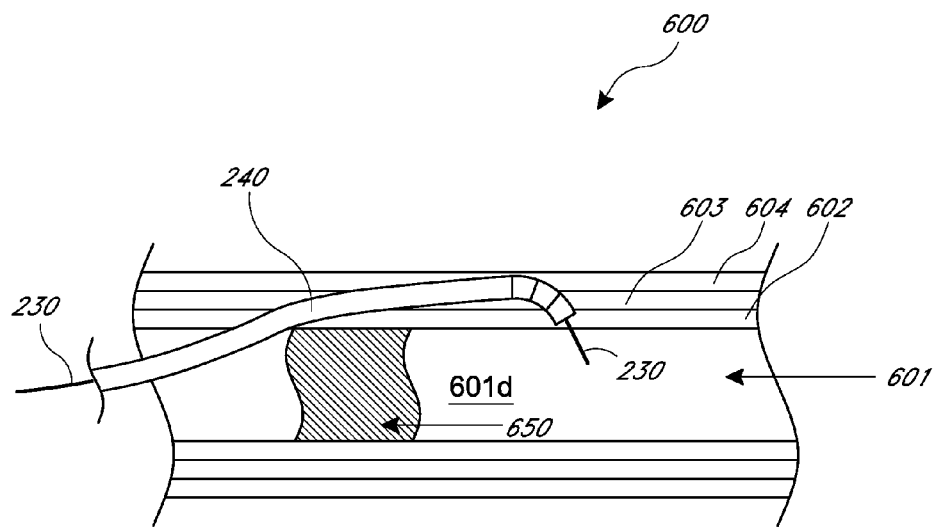

The next step of the method is illustrated in FIG. 19. An ultrasound transmission member 230 is advanced through the sheath 240. The ultrasound transmission member 230 may include a distal tip configured to penetrate tissue. The ultrasound transmission member 230 may be connected to a source of ultrasonic energy and configured such that ultrasonic vibrations can be transmitted to the tip of the ultrasound transmission member 230 to facilitate penetration of the vessel wall and/or to assist in re-entry from the subintimal space and into the distal central lumen 601*d*. As shown in FIG. 19, a distal portion of the ultrasound transmission member 230 has entered the distal central lumen 601*d* from the subintimal space.

Figure 20:
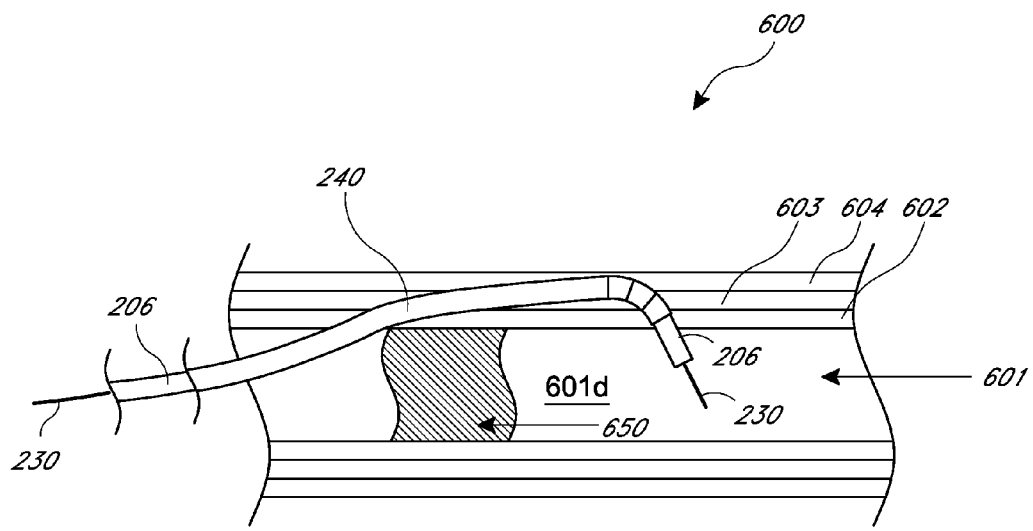

Turning to FIG. 20, the method continues by advancing the dilator 206 over the ultrasound transmission member 230, through the sheath 240, and into the distal central lumen 601*d*. The dilator 206 may have a distal portion having a similar profile to the ultrasound transmission member 230 such that the distal portion of the dilator 206 can facilitate the following of the ultrasound transmission member 230 from the extraluminal or subintimal space and into the central lumen 601. In this way, the dilator 206 serves as a transition member between the relatively small diameter of the ultrasound transmission member 230 and the relatively larger diameter of the sheath 240. In some embodiments, at least a portion of the dilator 206 is tapered in a direction towards the distal tip of the dilator 206.

In one embodiment, the dilator 206 is inserted into the sheath 240 before the ultrasound transmission member 230 is inserted. That is to say, after the guidewire 800 is removed from the sheath 240, the dilator 206 is advanced through the sheath 240. Next, the ultrasound transmission member 230 is advanced through the dilator 206. The ultrasound transmission member 230 can then be advanced through the extraluminal space so as to re-enter the distal central lumen 601*d* through the vessel wall.

In some embodiments, the dilator 206 and ultrasound transmission member 230 are sized such that the ultrasound transmission member 230 only advances outside the distal end of the dilator 206 by a maximum distance (for example, about 5 mm or less). For example, the ultrasound transmission member 203 and the dilator 206 can be sized and/or tapered in such a way that the ultrasound transmission member 203 extends beyond the end of the dilator 206 a predetermined amount before the walls of the dilator 206 prevent further advancement of the ultrasound transmission member 230. In this way, the dilator 206 can serve to prevent the ultrasound transmission member 230 from being advanced too far distally, thus minimizing the potential of the ultrasound transmission member 230 piercing the opposite vessel wall.

Figure 21:
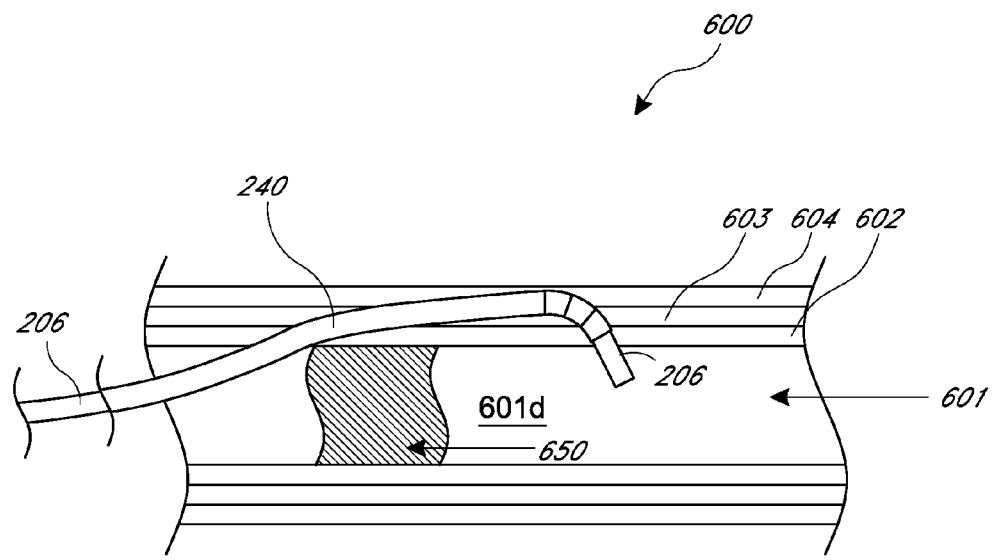
Figure 22:
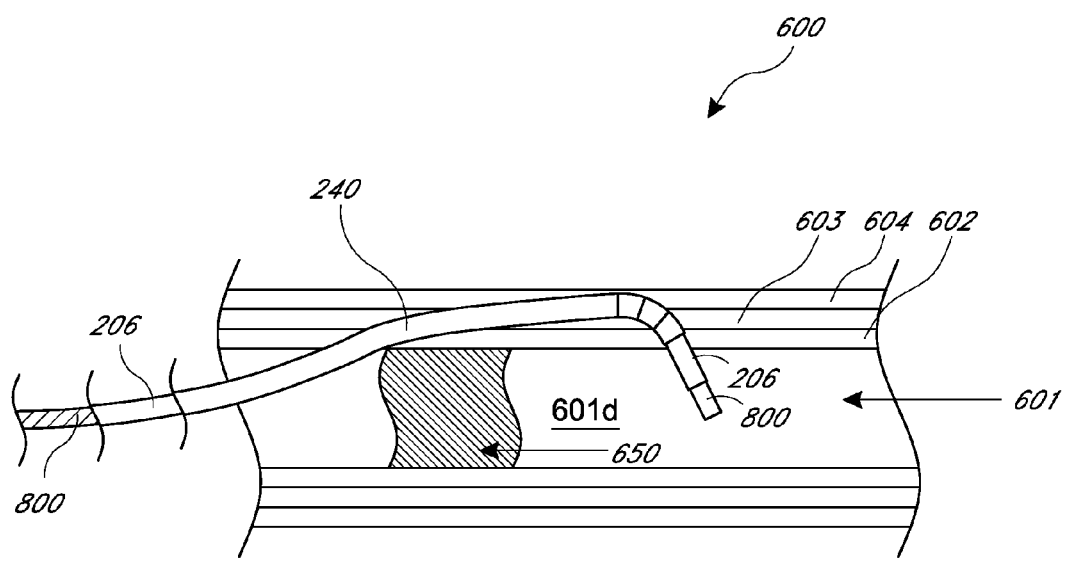
Figure 23:
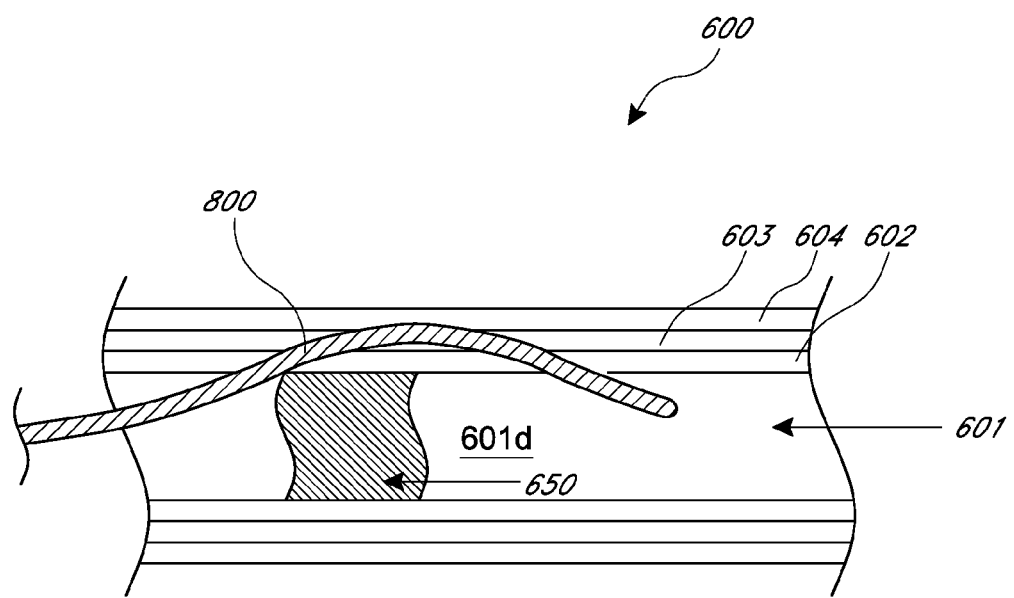

Turning to FIG. 21, the ultrasound transmission member 203 can be removed after the dilator 206 is positioned in the distal central lumen 601*d*. Next, as shown in FIG. 22, the guidewire 800 can be advanced through the dilator 206 and into the distal central lumen 601d. The sheath 240 and dilator 206 can then be removed as shown in FIG. 23 leaving the distal end of the guidewire 800 in the distal central lumen 601d. The sheath 240 and/or 206 dilator can be removed together or separately in any order.

Figure 24:
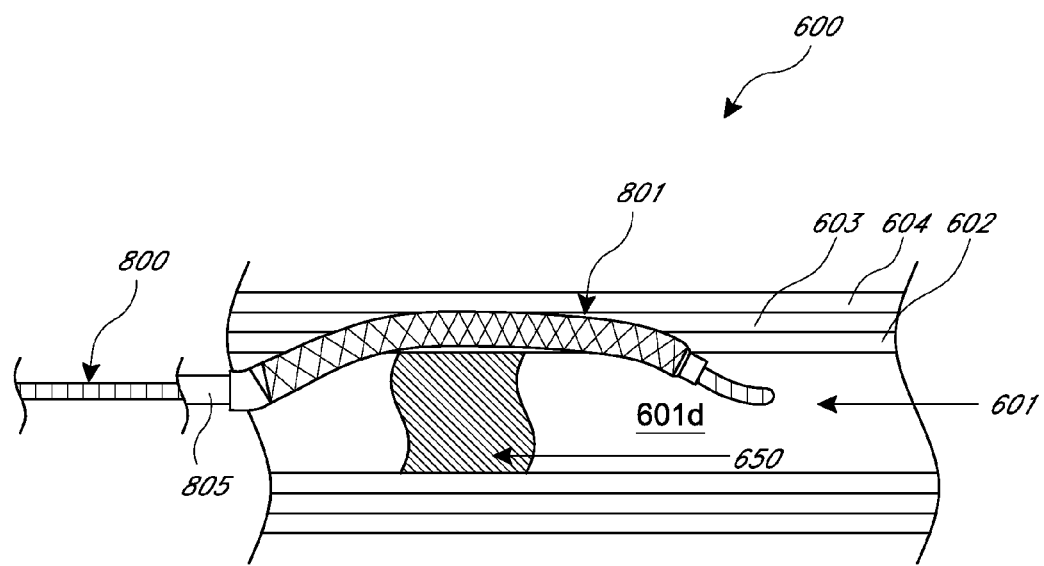
Figure 25:
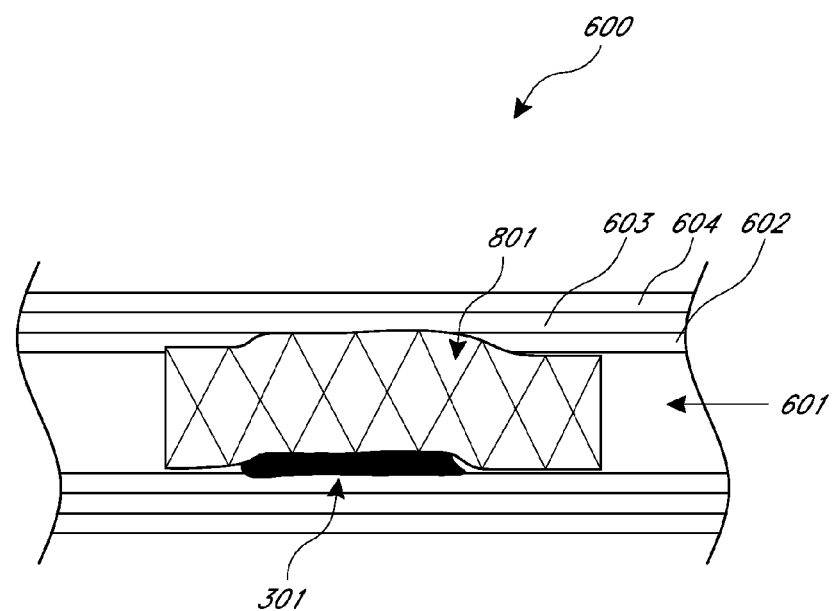

As shown in FIG. 24, once the guidewire 800 has crossed over the occlusion 650, a balloon catheter 805 with a stent 801 can be advanced over the guidewire 800 and positioned within the region of the occlusion 650. The balloon catheter 805 can then be expanded deploying the stent 801. The balloon catheter 805 and guidewire 800 can then be removed, leaving the fully deployed stent 805 in the vessel as shown in FIG. 25.

The various embodiments described above thus provide a number of ways to provide for treatment of occluded vessels. In addition, the techniques described may be broadly applied for use with a variety of medical procedures. Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and devices have been disclosed in the context of certain embodiments and examples, it will be understood by those skilled in the art that these techniques and devices may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein disclosed should not be limited by the particular disclosed embodiments described above, but should be determined only by a fair reading of the claims that follow.

What is claimed is:

1. An ultrasonic reentry device comprising:
    an elongate ultrasound transmission member having a proximal end coupled to a sonic connector and a distal end configured to penetrate a vessel wall;
    a catheter body having a distal end and at least one lumen extending longitudinally therethrough, the lumen surrounding at least a portion of the ultrasound transmission member;
    a dilator removably coupled to the catheter body and surrounding at least a portion of the ultrasound transmission member, the dilator having a length sized to expose at least a portion of the distal end of the ultrasound transmission member when the ultrasound transmission member is disposed within the dilator; and
    a sheath disposed over at least a portion of the dilator, the catheter body, and the ultrasound transmission member, wherein
    the sheath includes an articulating distal end configured to articulate up to about 90° away from a longitudinal axis, and
    the at least one lumen has an inner diameter and the dilator has an outer diameter sized to fit inside the inner diameter.

2. The device of claim 1 wherein the sheath has a length sized to expose at least a portion of a distal end of the dilator.

3. The device of claim 2, wherein the length of the dilator is sized to expose about 1-5 mm of the ultrasound transmission member.

4. The device of claim 1, wherein the at least one lumen has an inner surface that contacts an outer surface of the dilator.

5. An ultrasonic device for entering and exiting an extraluminal space of a vessel comprising:
    a catheter body having at least one lumen extending longitudinally therethrough; an elongate ultrasound transmission member extending longitudinally through the lumen, at least a portion of the ultrasound transmission member having an outer surface that tapers to a needle-like distal end;
    a dilator disposed over at least a portion of the ultrasound transmission member and configured to follow the ultrasound transmission member into the extraluminal space, at least a portion of the catheter body overlapping at least a proximal end of the dilator; and
    a sheath removably disposed over at least a portion of the dilator,
    wherein
    the sheath includes an articulating distal end,
    the needle-like distal end includes a rounded tip, and
    the dilator includes at least one portion tapered in a direction extending distally from the proximal end.

6. The device of claim 5, wherein a distal portion of the dilator has an internal diameter of about 0.01-0.002 inches.

7. A method of re-entering a central lumen of a vessel from an extraluminal space of the vessel, comprising:
    advancing a sheath over a guidewire positioned in the extraluminal space of the vessel;
    removing the guidewire;
    advancing an ultrasonic device having a distal end through the sheath;
    articulating at least a portion of the sheath towards the central lumen of the vessel;
    advancing a dilator through the sheath; and
    transmitting a vibration to the distal end of the ultrasonic device; and re-entering the central lumen of the vessel with the distal end of the ultrasonic device,
    wherein the dilator is sized to prevent the ultrasonic device from being advanced entirely through the dilator.

8. The method of claim 7, wherein the ultrasonic device comprises an ultrasound transmission member.

9. The method of claim 8, wherein the ultrasound transmission member includes a needle-like tip.

* * * * *